United States Patent [19]

Merslavic et al.

[11] Patent Number: 5,350,582
[45] Date of Patent: Sep. 27, 1994

[54] STABLE FORMULATION OF ENALAPRIL SALT, A PROCESS FOR THE PREPARATION THEREOF AND THE USE THEREOF

[75] Inventors: Marjo Merslavič, Straža; Jožica Ražen, Novo Mesto; Aleš Rotar, Ljubljana, all of Yugoslavia

[73] Assignee: Krka, torvana Zdravil, p.o., Mesto, Spratly Islands

[21] Appl. No.: 980,956

[22] Filed: Nov. 24, 1992

[30] Foreign Application Priority Data

Nov. 25, 1991 [YU] Yugoslavia .................. 1842/91

[51] Int. Cl.$^5$ .............................................. A61K 9/20
[52] U.S. Cl. ................................... 424/464; 424/465; 514/970
[58] Field of Search ................. 424/464, 465

[56] References Cited

U.S. PATENT DOCUMENTS 4,743,450  5/1988  Harris et al. .................. 424/440
4,830,853  5/1989  Murthy et al. ................. 424/440

Primary Examiner—Thurman K. Page
Assistant Examiner—James M. Spear
Attorney, Agent, or Firm—Pollock, Vande Sande & Priddy

[57] ABSTRACT

There is disclosed a stable formulation of enalapril salt of the formula I

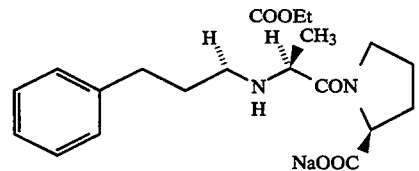

which is prepared in such manner that a compound of formula II

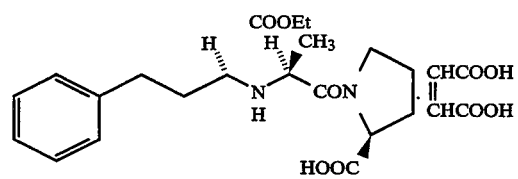

is suspended in demineralized water and a stoichiometric amount of the corresponding sodium compound such as sodium carbonate, sodium hydrogen carbonate or sodium hydroxide is added thereto, to this enalapril sodium salt prepared in situ of the formula I

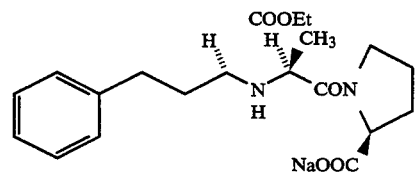

formulating additives are added, the whole is homogenized and formulated.

13 Claims, No Drawings

STABLE FORMULATION OF ENALAPRIL SALT, A PROCESS FOR THE PREPARATION THEREOF AND THE USE THEREOF

TECHNICAL FIELD

The present invention belongs to the field of pharmaceutical chemistry and relates to a stable formulation of enalapril salt of the formula I

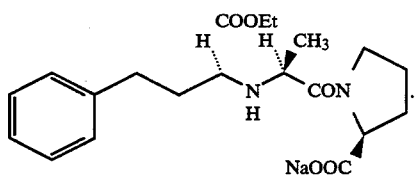

to a process or the preparation thereof as well as to the use thereof.

1. Technical Problem

There was a need to find a stable formulation of enalapril salt.

2. Prior Art

In the known formulations the active component is enalapril maleate. Such a formulation is e.g. disclosed in U.S. Pat. No. 4,374,829 in the form of capsules or tablets.

3. The Inventive Solution

The stable formulation of enalapril salt is prepared in such manner that a compound of formula II

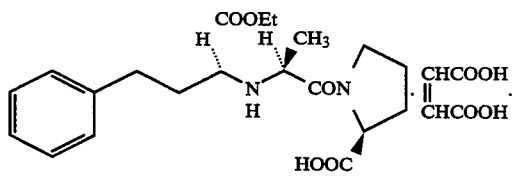

is suspended in demineralized water, a stoichiometric amount of the corresponding sodium compound such as sodium carbonate, sodium hydrogen carbonate or sodium hydroxide is added thereto, to this enalapril sodium salt prepared in situ of the formula I

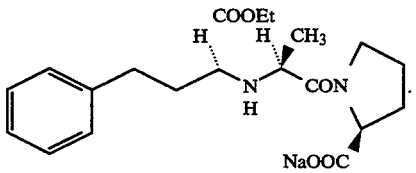

formulating additives are added, the whole is homogenized and formulated.

Formulating additives are e.g. cellulose, lactose of different sizes, alcohols, acids, bases, dyestuffs, starch, talc, polyvinyl pyrrolidone, magnesium stearate etc. Sodium salt may also be in combination with other antihypertensive agents (atenolol) and/or diuretics (hydrochlorothiazide).

The object of the invention is also a stable formulation of enalapril sodium salt obtained according to the above process, preferably in the form of tablets. Such a formulation has not been disclosed as yet.

Enalapril sodium salt of the formula I is a prodrug useful in the treatment of cardiovascular diseases, especially hypertension. It delivers the same active substance as any other prodrug having enalapril moiety in its molecule.

It should be pointed out that the stable formulation of enalapril according to the invention is designed in such a manner that enalapril maleate is temporarily converted into enalapril sodium salt. After the dissolution of such a formulation, especially a tablet, enalapril is liberated from the temporary form, enabling the absorption process to be carried out completely (see Example 8 and Graph 1).

Plasma concentrations determined after oral application of tablets prepared from 2.5 to 20 mg of enalapril maleate and having 2 to 16 mg enalapril in the form of sodium salt provide a therapeutical activity necessary for the treatment of the hypertension (see Example 9).

Daily doses amount to 4 to 64 mg of enalapril in the form of Na salt.

The invention is illustrated in detail by the following Examples, which should not be considered as a limitation thereof.

EXAMPLE 1

To enalapril maleate (250 g) suspended in demineralized water (800 ml), a solution of sodium hydroxide (60 g in 400 ml of demineralized water) was added. To thus prepared clear solution of enalapril sodium salt, corn starch (400 g) and dyestuff (30 g) were added and it was stirred until a homogeneously coloured mixture was obtained. To the homogeneously coloured mixture lactose 80 (3125 g) was added and the wet mass was dried at 40° to 50 ° C. Corn starch (125 g), talc (150 g) and magnesium stearate (43 g) were added to the dried mass and it was homogenized for 15 to 30 minutes. The homogenate thus prepared was used in preparing tablets.

EXAMPLE 2

To enalapril maleate (250 g) suspended in demineralized water (800 ml), a solution of sodium carbonate (81 g of $Na_2CO_3$ in 400 ml of demineralized water) was added. To thus prepared clear solution of enalapril sodium salt, corn starch (400 g) and dyestuff (30 g) were added and it was stirred until a homogeneously coloured mixture was obtained. To the homogeneously coloured mixture lactose 80 (3125 g) was added and the wet mass was dried at 40° to 50 ° C. Corn starch (125 g), talc (150 g) and magnesium stearate (43 g) were added to the dried mass and it was homogenized for 15 to 30 minutes. The homogenate thus prepared was used in preparing tablets.

EXAMPLE 3

To enalapril maleate (250 g) suspended in demineralized water (1200 ml), sodium hydrogen carbonate (125 g) was added in portions. To thus prepared clear solution of enalapril sodium salt, corn starch (400 g) and dyestuff (30 g) were added and it was stirred until a homogeneously coloured mixture was obtained. To the homogeneously coloured mixture lactose 80 (3125 g) was added and the wet mass was dried at 40° to 50 ° C. Corn starch (125 g), talc (150 g) and magnesium stearate (43 g) were added to the dried mass and it was homogenized for 15 to 30 minutes. The homogenate thus prepared was used in preparing tablets.

EXAMPLE 4

To enalapril maleate (200 g) suspended in demineralized water (1200 ml), a solution of sodium hydroxide (48 g in 400 ml of water) was added. To thus prepared clear solution of enalapril sodium salt, polyvinyl pyrrolidone K 25 (136 g), ethanol (400 g), corn starch (766 g) and dyestuff (24 g) were added and it was stirred until a homogeneously coloured mixture was obtained. To the homogeneously coloured mixture lactose 80 (5160 g) was added and the wet mass was dried at 40° to 50 ° C. Starch 1500 (200 g), talc (240 g) and magnesium stearate (68 g) were added to the dried mass and it was homogenized for 15 to 30 minutes. The homogenate thus prepared was used in preparing tablets.

EXAMPLE 5

To enalapril maleate (200 g) suspended in demineralized water (1600 ml), sodium hydrogen carbonate (100 g) was added in portions. To thus prepared clear solution of enalapril sodium salt polyvinyl pyrrolidone K 25 (136 g), ethanol (400 g), corn starch (766 g) and dyestuff (24 g) were added and it was stirred until a homogeneously coloured mixture was obtained. To the homogeneously coloured mixture lactose 80 (5160 g) was added and the wet mass was dried at 40° to 50 ° C. Starch 1500 (200 g), talc (240 g) and magnesium stearate (68 g) were added to the dried mass and it was homogenized for 15 to 30 minutes. The homogenate thus prepared was used in preparing tablets.

EXAMPLE 6 (COMPARATIVE)

A mixture of enalapril maleate (200 g), polyvinyl pyrrolidone K 25 (136 g), corn starch (766 g), dyestuff (24 g) and sodium hydrogen carbonate (100 g) was stirred until a homogeneously coloured mixture was obtained. To the homogeneously coloured mixture lactose 80 (5160 g), starch 1500 (200 g), talc (240 g) and magnesium stearate (68 g) were added and it was homogenized for 15 to 30 minutes. The homogenate thus prepared was used in preparing tablets.

EXAMPLE 7

Stability Test

Stability studies were made with tablets of Examples 5 and 6 under conditions as disclosed in Table 1. The content of enalapril sodium salt (NaE) and the presence of decomposition product 2-(1-ethoxycarbonyl-3-phenylpropyl-3-methyl-hexahydropyrrolo)-[1,2-a]-pirazine-1,4-dione (DKP) were controlled.

TABLE 1

| | Stability of enalapril sodium salt in tablets | | | |
|---|---|---|---|---|
| | NaE | Example 5 content in % DKP | EM + NaHCO₃ | Example 6 content in % DKP |
| initial content | 100.0 | <0.1 | 98.8 | 0 |
| RT 3 months | 100.0 | <0.1 | 97.5 | 2.1 |
| 35° C. 3 months | 98.7 | 0.1 | 85.5 | ~10.0 |
| 50° C. 3 months | 94.2 | 4.2 | 13.8 | ~80.0 |
| 31° C. 70% RH 3 months | 100.0 | <0.1 | 92.0 | ~10.0 |
| 37° C. 85% RH 3 months | 98.9 | 0.5 | 70.9 | ~30.0 |

RT = room temperature
RH = relative humidity

From the above Table it is evident that the enalapril sodium salt prepared in situ is more stable in a pharmaceutical formulation than in case of only physical mixing of enalapril maleate and sodium hydrogen carbonate (EM+NaHCO₃), i.e., enalapril maleate/(NaHCO₃).

EXAMPLE 8

Dissolution Test

Tablets prepared according to Examples 5 and 6 were tested for their dissolution characteristics. A standard method (USP XXII) was used to evaluate the dissolution profiles. The results are presented in Graph 1 in % of enalapril maleate dissolved.

EXAMPLE 9

Plasma Levels of Enalaprilate

After p.o. application of tablets with 6 mg of enalapril in the form of sodium salt, plasma samples were analysed. The following enalaprilate concentrations were determined.

| time (h) | concentration (μg/l) |
|---|---|
| 0 | 0 |
| 0.5 | 1.22 |
| 1 | 13.99 |
| 2 | 63.13 |
| 3 | 84.07 |
| 4 | 68.64 |
| 6 | 49.63 |
| 8 | 27.30 |
| 12 | 14.36 |
| 24 | 2.73 |

We claim:
1. Process for preparing stable formulation of enalapril sodium salt of the formula I

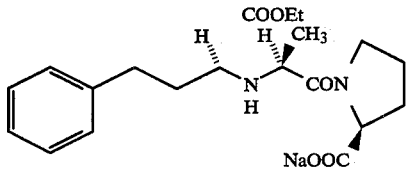

characterized in that enalapril mileate of formula II

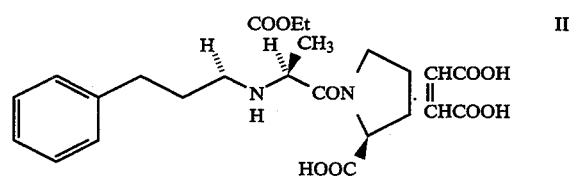

is suspended in demineralized water and a stoichiometric amount of the corresponding sodium compound selected from the group consisting of sodium carbonate, sodium hydrogen carbonate and sodium hydroxide is added thereto, to this enalapril sodium salt prepared in situ of the formula I

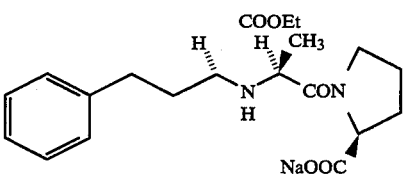

formulating additives are added, the whole is homogenized and formulated.

2. Stable formulation of enalapril sodium salt obtained according to the process of claim 1.

3. Formulation according to claim 2, characterized in that it is in the form of a tablet.

4. Pharmaceutical composition comprising an effective amount of enalapril sodium of formula 1

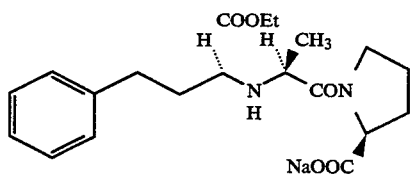

obtained in accordance with the process of claim 1.

5. A method for treating cardiovascular disease which comprises administering to a patient suffering from cardiovascular disease a pharmaceutical composition comprising an effective amount for treating cardiovascular disease of enalapril sodium of formula 1

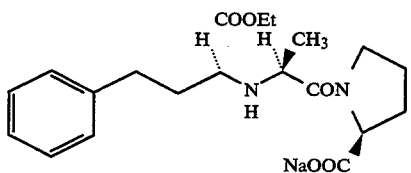

obtained in accordance with the process of claim 1.

6. The method of claim 5 wherein said cardiovascular disease is hypertension.

7. The method of claim 5 wherein said pharmaceutical composition is a tablet.

8. The method of claim 7 wherein said tablet contains 2 to 16 mg of said enalapril sodium.

9. The method of claim 5 wherein the daily dosage of said enalapril sodium is 4 to 64 mg.

10. The process of claim 1 which further comprises drying at 40° C. to 50°, subsequent to adding said sodium compound.

11. The composition of claim 4 being in the form of a tablet.

12. The composition of claim 11 wherein said tablet contains 2 to 16 mg of said enalapril sodium.

13. The composition of claim 4 which further comprises at least one member selected from the group consisting of cellulose, lactose, alcohol, acid, base, dyestuff, starch, talc, polyvinyl pyrolidone and magnesium stearate.

* * * * *

UNITED STATES PATENT AND TRADEMARK OFFICE
CERTIFICATE OF CORRECTION

PATENT NO. : 5,350,582
DATED : September 27, 1994
INVENTOR(S) : Merslavic, et al It is certified that error appears in the above-indentified patent and that said Letters Patent is hereby corrected as shown below:

On the title page, item [75] the home country of all of the inventors should read —all of Slovenia— not all of Yugoslavia.

Signed and Sealed this

Thirteenth Day of June, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,350,582
DATED      : September 27, 1994
INVENTOR(S) : Merslavic, et al.

It is certified that error appears in the above-indentified patent and that said Letters Patent is hereby corrected as shown below:

On title page, item [73] Assignee:  should read --KRKA, tovarna zdravil, p.o., Novo mesto, SLOVENIA--

Signed and Sealed this

Ninth Day of July, 1996

Attest:

BRUCE LEHMAN

Attesting Officer

Commissioner of Patents and Trademarks